United States Patent [19]

Shevel

[11] Patent Number: 5,938,436
[45] Date of Patent: Aug. 17, 1999

[54] ORAL PROSTHESIS

[75] Inventor: Elliot J. Shevel, Randburg, South Africa

[73] Assignee: Fairbairn Reads Trust Company Limited as Trustees of the Eureka Trust, St. Peter's Port, United Kingdom

[21] Appl. No.: 08/870,496

[22] Filed: Jun. 6, 1997

Related U.S. Application Data

[63] Continuation-in-part of application No. 08/611,183, Mar. 5, 1996, abandoned.

[51] Int. Cl.$^6$ .................................................. A61C 3/00
[52] U.S. Cl. ................................................ 433/6; 128/860
[58] Field of Search ..................... 433/6, 7, 215; 128/848, 859, 860

[56] References Cited

U.S. PATENT DOCUMENTS

| | | |
|---|---|---|
| 3,219,033 | 11/1965 | Wallshein . |
| 3,259,129 | 7/1966 | Tepper ...................................... 433/6 X |
| 3,277,892 | 10/1966 | Tepper ...................................... 433/6 X |
| 3,884,226 | 5/1975 | Tepper . |
| 4,253,828 | 3/1981 | Coles et al. . |
| 4,273,530 | 6/1981 | Broussard . |
| 4,299,568 | 11/1981 | Crowley ...................................... 433/6 |
| 4,413,978 | 11/1983 | Kurz . |
| 4,553,549 | 11/1985 | Pope et al. . |
| 4,784,605 | 11/1988 | Bergersen ................................... 433/6 |
| 4,986,283 | 1/1991 | Tepper ................................ 128/860 X |
| 5,085,584 | 2/1992 | Boyd . |
| 5,096,416 | 3/1992 | Hulsink ...................................... 433/6 |

*Primary Examiner*—Nicholas D. Lucchesi
*Attorney, Agent, or Firm*—Fish & Richardson P.C.

[57] ABSTRACT

The invention provides an oral prosthesis in the form of a dental plate which fits against the inside of a user's teeth. The plate when fitted projects from the teeth toward the user's tongue. The extent of the projection, and the thickness of the plate, is selected to displace the tongue in a predetermined manner.

4 Claims, 2 Drawing Sheets

ORAL PROSTHESIS

This application is a continuation-in-part of Ser. No. 08/611,183 filed Mar. 5, 1996, now abandoned.

FIELD OF THE INVENTION

This invention relates to an oral prosthesis.

BACKGROUND TO THE INVENTION

Headaches and similar ailments can be caused by the position of the lower jaw in relation to the upper jaw. Also, the position of the tongue in the mouth can affect the position of the jaws.

OBJECT OF THE INVENTION

It is an object of this invention to provide an oral prosthesis which can cause the tongue and mandible of a user wearing the prosthesis to be displaced from its normal position in a predetermined manner.

SUMMARY OF THE INVENTION

In accordance with this invention there is provided an oral prosthesis comprising a dental plate having edges shaped to locate in use against the inside surface of teeth of a lower jaw, the plate projecting from the shaped edges operatively inwardly to abut or locate under a user's tongue, the extent of the projection, and the thickness of the plate, being selected to displace the tongue in use in a predetermined manner.

The invention also provides an oral prosthesis comprising a dental plate having edges shaped to locate in use against the inside surface of teeth of an upper jaw, the plate projecting from the shaped edges operatively inwardly to abut a user's tongue, the extent of the projection, and the thickness of the plate, being selected to displace the rear of the tongue in use in a predetermined manner.

A further feature of the invention provides for the plate to be shaped to permit the tip of the user's tongue to contact the front of the user's palate.

A still further feature of the invention provides for the plate to extend over the palate between molars on opposite sides of the jaw.

Preferably the selection is made in order to displace the jaw in a manner that causes relaxation of the primary jaw muscles of a user. Preferably also, the plate is removable, and may have clips or the like to maintain it in position.

BRIEF DESCRIPTION OF THE DRAWINGS

A preferred embodiment of the invention is described by way of example only, and with reference to drawings, in which.

DETAILED DESCRIPTION OF THE INVENTION

Figure 1:
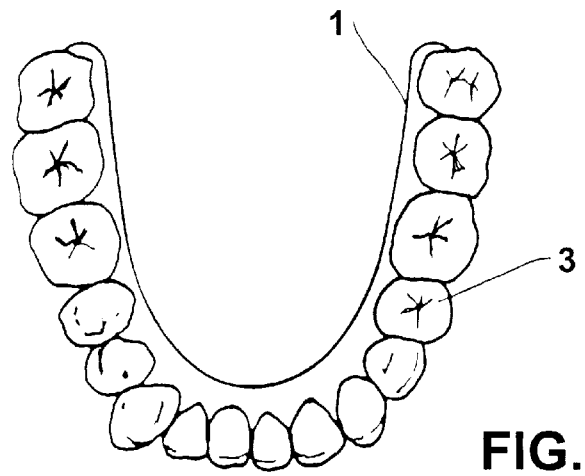
FIG. 1 is a sketch of the plan view of the teeth in a lower jaw with an oral prosthesis according to the invention in position.
Figure 2:
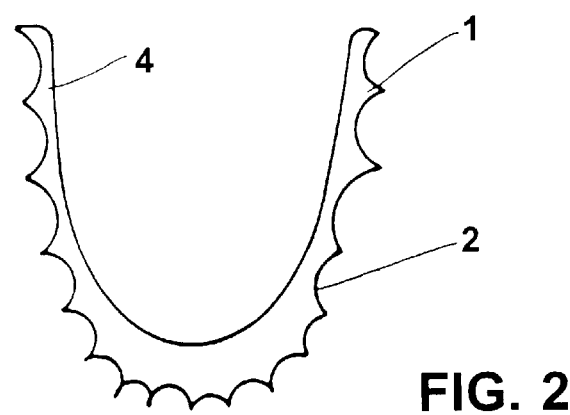
FIG. 2 & FIG. 3 are plan and oblique views respectively, of the oral prosthesis of FIG. 1.
Figure 3:
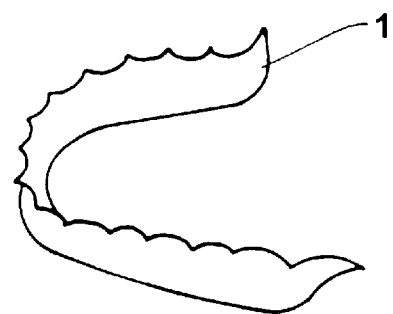

As illustrated in FIGS. 1 to 3, an oral prosthesis for a lower jaw is shown in the form of a plate (1), having a shaped outer edge (2), formed to be located against the inner surface of a set of teeth (3) of a lower jaw (FIG. 1). The plate is thus generally "U"-shaped and its inner surface (4) projects away from the inside surface of the teeth into the cavity of the lower jaw. The extent of this projection over the gums and slightly under the tongue, as well as the thickness of the plate in various positions around the extent thereof, is selected according to experience and knowledge of anatomy. Clips (5) assist in securing the plate in position.

Figure 4:
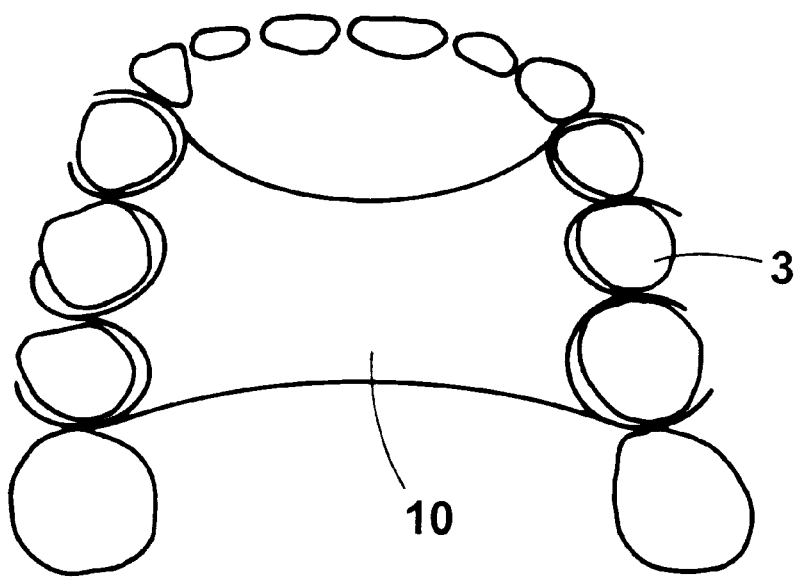
FIG. 4 is a sketch of the plan view of the teeth in an upper jaw with an oral prosthesis according to the invention in position.
Figure 5:
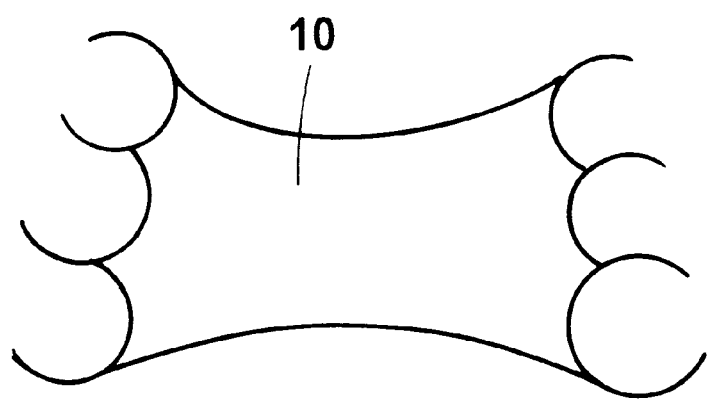
FIG. 5 is a plan view of the oral prosthesis of FIG. 4.

As illustrated in FIGS. 4 and 5, a plate (10) can also be formed to be located in use against the inner surface of a set of teeth (4) of an upper jaw (FIG. 4). The plate locates against the molars on either side of the jaw and extends across the palate. The plate does not locate against the front teeth and permits the tip of the tongue to contact the front of the palate, so as not to interfere with speech. This in turn allows the plate to be worn in the day time as well as at night which makes the plate effective for 24 hours a day.

The position of the tongue can be adjusted by the presence of the plate, and thus the position of the jaws can be altered by moving the tongue.

The jaw position may be altered to relax jaw muscles, and this can relieve associated and referred pain. The plate is made, generally speaking, in accordance with well known techniques for forming and producing dental prostheses. The position of any thickening or extent need not be uniform around the periphery of the operative position, and the plate will often require final adjustment to the thickness and/or the extent of projection into the mouth cavity, to achieve optimal results.

Normally, when a person is relaxed, the tip of the tongue rests lightly against the front of the palate just behind the upper teeth. The remainder of the tongue does not touch the palate and there is a space between the tongue and the palate furthest back. The position of tongue influences the position of the lower jaw, which in turn impacts on the amount of tension in the muscles at the side of the head which are responsible for controlling the posture of the lower jaw. In patients with headaches of muscular origin, the muscles at the side of the head contract as a response to stress and tension, and the lower jaw is consequently displaced from its proper rest position. As the lower jaw is elevated, the tongue is in turn elevated and the resting space between the tongue and palate is reduced. By inducing the tongue to assume its proper rest position, relaxation of the muscles which caused the headaches is achieved.

The prosthesis of the invention for an upper jaw is thus contoured to fit the resting space between the tongue and the palate exactly so that the tongue is encouraged to resume its natural rest position. This is achieved by ensuring that the patient's tongue does not touch the prosthesis during speech. Conveniently, the patient is made to speak with the prosthesis in the mouth and then the prosthesis is ground away until there is no contact between the tongue and the prosthesis during speech. Once this is achieved, the prosthesis is the correct shape. If the prosthesis is even slightly too thick, the tongue is displaced to a position lower than its normal rest position and the prosthesis will not work. It is thus important that the prosthesis for use in the upper jaw does not cover the front of the palate as this is where the tongue would normally rest in the relaxed position. If this area were to be covered, the tongue would be depressed below its normal rest position causing the muscles at the side of the head to lengthen beyond the ideal resting length. Experience has shown that when this occurs, the muscles remain painful and the headaches do not improve. On the contrary, this can often lead to headaches being aggravated.

These embodiments of the invention are further exemplified in the clinical histories given below.

Clinical History 1

Patient A was examined and complained of "deep, dull, unbearable pain" behind the eyes, in the frontal region, and over the temples, occipital regions and neck. The pain occurred with a frequency of 3–4 times a week, and lasted between 2 and 24 hours. The patient first experienced these symptoms at the age of 25 years and was 55 years old at the time of examination. The pain was made worse by stress and certain foodstuffs.

Clinical examination and diagnostic tests revealed the cause of his pain to originate in a trigger area in the antero-superior fibers of the temporalis muscles, and was most probably related to stress. The object of treatment with an embodiment of the invention, was to encourage relaxation of the temporalis muscles.

The prosthesis was molded and prepared, and fitted. It initially caused a slurring of the patient's speech, particularly when pronouncing the letter "S". The anterior portion of the plate in the midline was trimmed down until it no longer caused any speech impediment. This is necessary, and clinical experience has shown that if the plate is too thick it can cause an intensification of symptoms. Some three weeks later, the patient was completely symptom free.

Clinical History 2

The patient complained of severe and chronic headaches which started in 1988, but which intensified two years ago following an attack of encephalitis. The headaches occurred every 6 to 7 days, and were made worse by loud noises, "episodes of sinusitis" and by hormonal changes occurring during menstruation. However, a radiologist's report showed the sinuses to be clear.

It has been found that patients frequently mistakenly believe their headaches are caused by sinusitis, because of the distribution of their pain over the frontal and maxillary sinuses. With proper diagnostic procedures, the pain can often be found to originate from the muscles of mastication.

The origin of the patient's pain on clinical examination and diagnostic testing was found to be the anterior fibers of the masseter muscles and the digastric muscles. To cause relaxation in the muscles, the mandible has to be repostured not only lower, but also slightly forward.

A prosthesis was prepared to act as a shim between the lower teeth and longual mandibular gingival surface on the one hand, and the sensitive ventral surface of the tongue on the other. The action was designed to separate the lower jaws slightly from the tongue, and as the tongue cannot position itself higher in the mouth because of its relationship to the palate, the net result is designed to cause the mandible to reposition itself slightly lower.

The positioning of the anterior portion of the plate between the anterior part of the ventrum of the tongue and the anterior teeth, caused the mandible to be postured slightly forward, relieving tension in the digastric muscles. Sixteen days after fitting, there was a follow up consultation during which the plate was thickened by some 2 mm with good results. The patient estimates a reduction in symptoms of some 80%.

The final shape of the prosthesis has to be determined by clinical examination and trial and error. The exact degree of relaxation and movement of the jaw has to be established during follow up consultations, and with reference to symptomatic response.

It is considered that the invention provides a simple oral prosthesis for altering jaw posture. If necessary clips can be provided to retain the plate in position, and these clips will be positioned between suitable gaps in the teeth so as not to affect the teeth themselves. Unlike the commonly used appliance called a "bite plate", which is specifically designed to change the patient's occlusion when worn, the prosthesis of the inventor is designed not to affect the occlusion at all, but rather to change the posture of the tongue. The prosthesis of the invention, therefore, does not interfere with a person's bite, is comfortable to use, and can be worn during eating and speaking.

What I claim as new and desire to secure by Letters Patent is:

1. An oral prosthesis comprising a dental plate having edges shaped to locate in use against the inside surface of teeth of an upper or lower jaw, the plate projecting from the shaped edges operatively inwardly to abut a user's tongue, said plate including means for displacing the rear of the tongue in use in a predetermined manner, and the dental plate further including means for allowing the tip of the user's tongue to contact the front of the user's palate.

2. An oral prosthesis as claimed in claim 1 in which the dental plate extends over the palate between molars on opposite sides of the jaw.

3. An oral prosthesis as claimed in claim 1 wherein said plate displaces the jaw in a manner that causes relaxation of the primary jaw muscles of a user.

4. An oral prosthesis as claimed in claim 1 in which the plate has clips to maintain it in position.

\* \* \* \* \*